United States Patent
Crabb

(10) Patent No.: US 9,351,867 B2
(45) Date of Patent: *May 31, 2016

(54) METHOD OF TREATING PROLAPSE OF A VAGINA

(71) Applicant: Coloplast A/S, Humlebaek (DK)

(72) Inventor: Rachael Anne Bergstrom Crabb, St Paul, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/698,868

(22) Filed: Apr. 29, 2015

(65) Prior Publication Data

US 2015/0245942 A1 Sep. 3, 2015

Related U.S. Application Data

(63) Continuation of application No. 14/458,262, filed on Aug. 13, 2014, now Pat. No. 9,084,661, which is a continuation of application No. 13/766,789, filed on Feb. 14, 2013, now Pat. No. 8,834,348.

(30) Foreign Application Priority Data

Mar. 13, 2013 (EP) .................................. 13158926

(51) Int. Cl.
*A61F 2/00* (2006.01)
*A61F 6/12* (2006.01)

(52) U.S. Cl.
CPC ................ *A61F 6/12* (2013.01); *A61F 2/0009* (2013.01); *A61F 2/0063* (2013.01); *A61F 2/0077* (2013.01); *A61F 2/0022* (2013.01); *A61F 2/0045* (2013.01); *A61F 2002/0072* (2013.01); *A61F 2210/0004* (2013.01); *A61F 2220/0075* (2013.01); *A61F 2230/0015* (2013.01); *A61F 2230/0067* (2013.01); *A61F 2230/0093* (2013.01); *A61F 2250/0031* (2013.01); *A61F 2250/0063* (2013.01)

(58) Field of Classification Search
CPC ....... A61F 2/00; A61F 2/0045; A61F 2/0005; A61F 2/0009; A61F 2/0063
USPC .................................................. 600/29–32, 37
See application file for complete search history.

(56) References Cited

U.S. PATENT DOCUMENTS

| | | | |
|---|---|---|---|
| 8,109,867 B2 * | 2/2012 | Rosenblatt | A61F 2/0063 600/30 |
| 8,834,348 B2 * | 9/2014 | Crabb | A61F 2/0009 600/30 |
| 9,084,661 B2 * | 7/2015 | Crabb | A61F 2/0009 |
| 2009/0005867 A1 * | 1/2009 | Lefranc | A61F 2/0045 623/11.11 |

* cited by examiner

*Primary Examiner* — John Lacyk
(74) *Attorney, Agent, or Firm* — Coloplast Corp., Coloplast A/S; Nick Baumann

(57) ABSTRACT

A method of treating prolapse of a vagina includes inserting a shell into the vagina; contacting a convex exterior apex of the shell with an interior apical portion of the vagina; and securing a first portion of an anchor to the shell and securing a second portion of the anchor to a ligament or a sacrum exterior to and separate from the vagina.

18 Claims, 14 Drawing Sheets

METHOD OF TREATING PROLAPSE OF A VAGINA

BACKGROUND

Pelvic organs are those located inside of the pelvis and include the vagina, the uterus, the bladder, and the rectum. The pelvic floor (inferior) forms the foundation of support for the pelvic organs and the organs are supported from above (superior) by ligaments and other connective tissue.

Some women experience a decrease in support to the pelvic organs. A decrease in pelvic organ support is sometimes attributed to child birth, hysterectomy, or to the natural aging process. Decreased pelvic organ support can contribute to one or more of the pelvic organs prolapsing from its natural position in the pelvis toward, or even through, the inferior pelvic floor. This condition is referred to as pelvic organ prolapse, and some women choose to have the condition treated through surgical intervention.

Surgeons and patients would welcome advances in the treatment of pelvic organ prolapse.

SUMMARY

One aspect provides a system for treating pelvic organ prolapse including a plug, a skirt, and an anchor. The plug includes a base opposite an apex with the base wider than the apex. An exterior surface of the apex is shaped to conform to an interior apical portion of a vagina. The skirt is attachable to the plug and includes multiple pores that are sized to allow tissue of the interior apical portion of the vagina to grow through the skirt. The anchor has a proximal portion that is insertable through the vagina and the skirt for attachment to the apex of the plug. The anchor has a length that allows a distal portion of the anchor to be attached to a sacrum of a patient.

One aspect provides a system for treating pelvic organ prolapse including a porous sheet of material, a plug, and an anchor. The porous sheet of material is positionable on an interior apical portion of a vagina. The plug is made of biodegradable material and is insertable into the vagina. The plug includes a body portion having a convex hemispherical shape that is configured to press the porous sheet of material into direct contact with the interior apical portion of a vagina. The plug is provided with a hole formed at a distal apex of the plug. The anchor has a proximal portion that is insertable into the hole formed at the distal apex of the plug, and a length that allows a distal portion of the anchor to be attached to a sacrum of a patient.

One aspect provides a system for treating pelvic organ prolapse including a shell and an anchor. The shell is made of biodegradable material that is insertable into a vagina. The shell has a convex exterior apex that is sized to contact an interior apical portion of the vagina. The anchor has a proximal portion that is attachable to the apex of the shell and a distal portion that is provided with a tissue fixation device that is attachable to tissue exterior the vagina such that the anchor and the shell combine to support and elevate the interior apical portion of a vagina.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
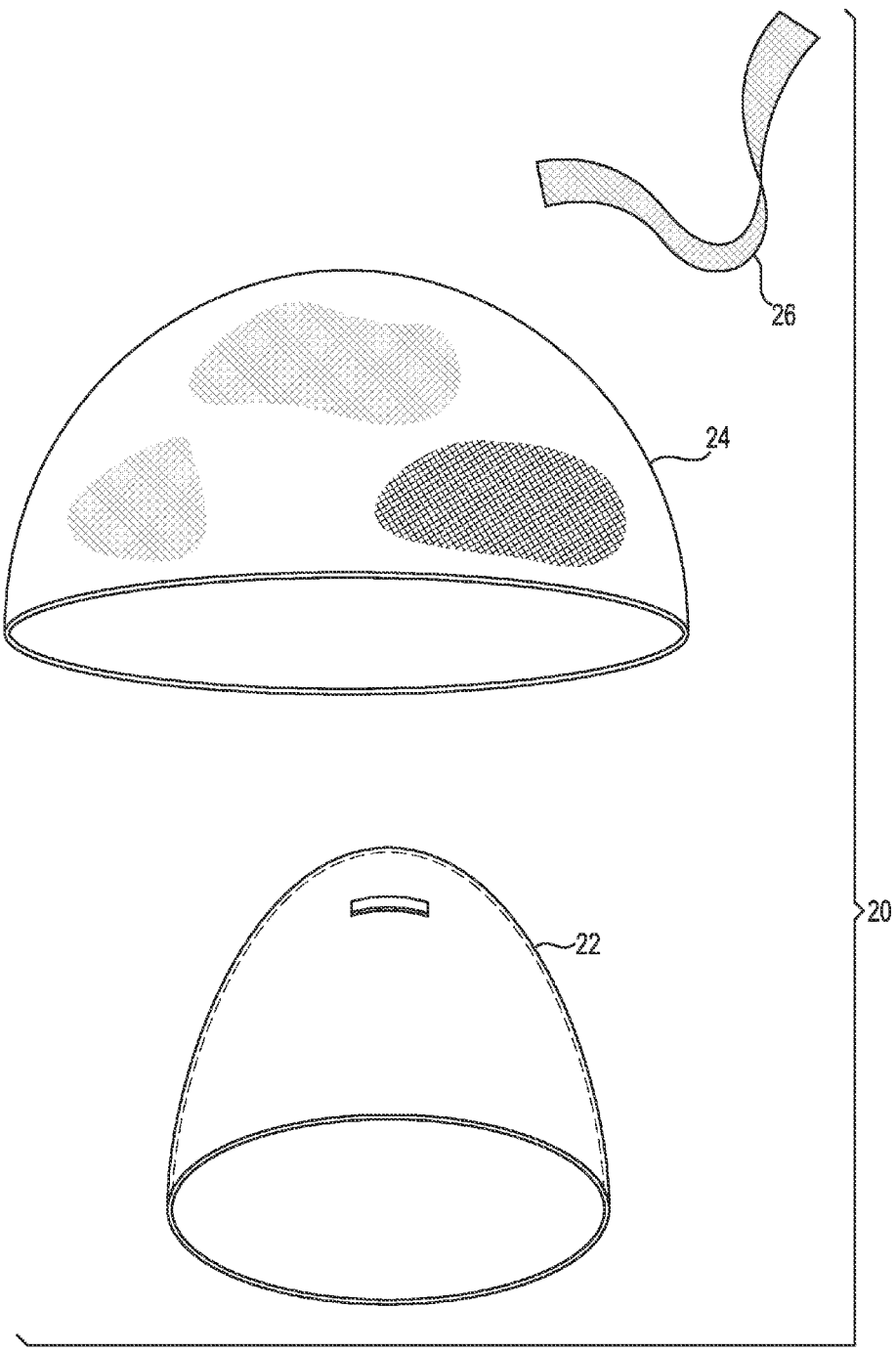
FIG. 1 is a perspective view of one embodiment of a system for treating pelvic organ prolapse.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

Individuals have anatomy of different sizes. For example as regards females, the vaginal vault can vary in length (depth). Some women having had a hysterectomy will have had all or some of the cervix removed (e.g., a cervical stump is at times left in place at the apex of the vagina).

This application relates to the surgical treatment of pelvic organs that are susceptible to prolapse through the inferior pelvic floor. Embodiments provide the surgeon with access to the apex of the vagina through the natural vaginal opening.

With this in mind, in this application the term "proximal" means that orientation that is closest to the surgeon in contrast to the term "distal" which means that orientation farthest from the surgeon. For example, the natural vaginal opening is located proximal to the apex of the vagina.

The surgical intervention to treat vaginal pelvic organ prolapse typically includes a support material that is attached proximally to an outside, exterior surface of the vagina and distally to the sacrum of the patient. For example, one suitable approach of treating vaginal prolapse includes attaching two adjacent and splayed legs of a Y-shaped support to the exterior surface of the vagina followed by the attachment of the remaining base portion of the Y-shaped support to the sacrum. This approach pulls the exterior surface of the apex of the vagina toward the sacrum and has proved to be effective in treating vaginal prolapse.

Embodiments described in this application provide a system for treating pelvic organ prolapse that provides internal support to the prolapsed organ. Embodiments provide a skirt of material that is inserted through the natural vaginal opening inward to the interior apical cuff of the vagina. A plug is provided that is inserted into the vagina to hold the skirt in contact with the interior wall the vagina in the region of the apical cuff. The plug ensures that the skirt remains in contact with the interior wall the vagina, which encourages and promotes tissue growth through the skirt. The skirt and the plug are secured to an anchor that extends from the plug (through the skirt and the wall of the vagina) to supporting tissue outside of the vagina, for example to the sacrum or ligaments attached to the sacrum.

In one embodiment, the plug is configured to biodegrade after tissue grows through the skirt.

In one embodiment, the plug and the skirt are configured to biodegrade after tissue growth is stimulated in the region of the skirt.

In one embodiment, the plug, the skirt, and the anchor are all configured to biodegrade after tissue growth occurs to support the vagina.

FIG. 1 is a perspective view of one embodiment of a system 20 for treating pelvic organ prolapse. The system 20 includes a plug 22, a skirt 24, and an anchor 26.

The skirt 24 is porous and sized to be inserted inside of the vagina, and after prolonged contact with the tissue of the vagina, tissue will eventually grow through the skirt 24. The skirt 24 is configured to be flexible (or drapeable) for improved conformance to the interior of the vagina. After implantation, the skirt 24 provides a resilient and durable support structure composed of tissue/skirt 24.

The plug 22 is inserted into the vagina after the skirt 24 has been placed. The plug 22 is configured to apply pressure to the skirt 24 to ensure contact between the skirt 24 and the internal tissue surfaces of the vagina. One embodiment of the plug 22 is sized and shaped to mimic the mucous plug that forms at the vagina/cervix interface during pregnancy. Other shapes for the plug 22 that are different from the shape of a mucosal plug are also acceptable. In one embodiment, the plug 22 is provided as a thin-walled shell that is insertable into the vagina, where the shell has a convex exterior apex that is sized to contact an interior apical portion of the vagina.

The anchor 26 is sized to have one end portion attached to both the plug 22 and the skirt 24 inside of the vagina and a second end portion that extends outside the vagina to a suitable supporting tissue, such as a ligament or another tough structure. In this manner, system 20 allows the vagina to be supported across the entirety of its interior apical surface, which provides for a more natural conformation and improved distribution of the supporting forces applied to the vagina. In one embodiment, the plug 22 is configured to biodegrade out of the vagina leaving the anchor 26 attached to the skirt 24 at one end and attached at the other end to the supporting tissue.

Figure 2:
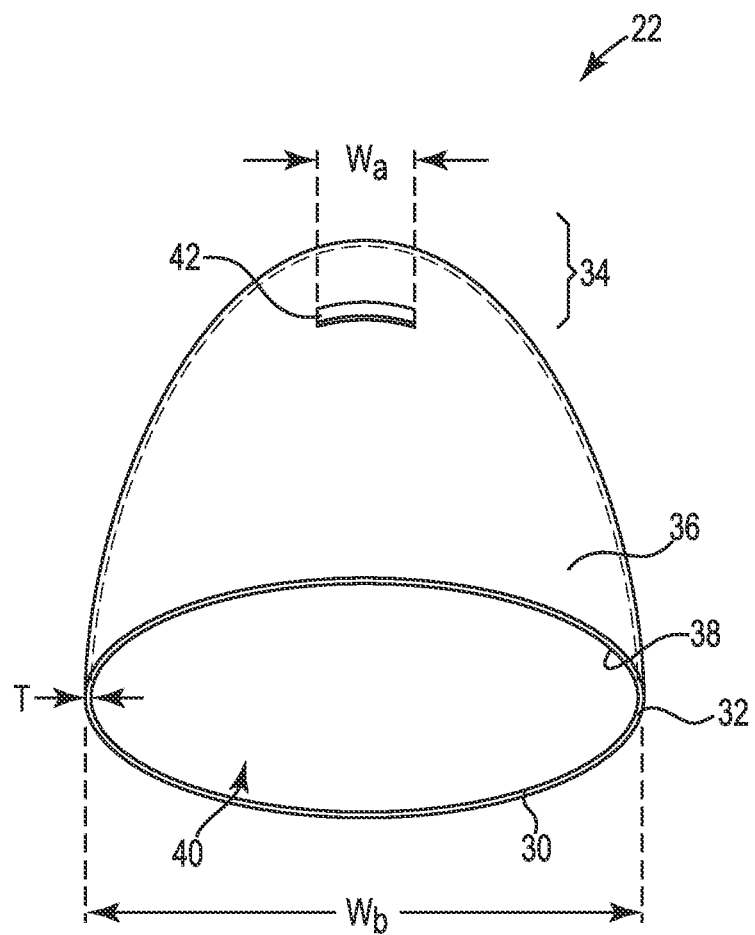
FIG. 2 is a perspective view of one embodiment of a plug of the system illustrated in FIG. 1.

FIG. 2 is a perspective view of one embodiment of the plug 22. The plug 22 includes a wall 30 that forms a hollow hemispherical cap extending between a base 32 and an apex 34. The apex 34 has a curved shape that is sized to conform to the interior apical surface of the vagina. In one embodiment, the apex 34 is a convex hemispherical distal nose of the plug 22 and is configured to maintain the porous skirt 24 in contact with an interior apical portion of a vagina. In this embodiment, the plug 22 (or hollow hemispherical cap) has a convex outside surface 36, a concave inside surface 38, and the wall 30 has a wall thickness T. In one embodiment, the wall thickness T is substantially uniform with a dimension between 0.2-2.0 cm. Embodiments provide for a more elliptically shaped the plug 22.

In one embodiment, the plug 22 is a biodegradable plug. Biodegradable means that the plug 22 will degrade from a solid intact material to constituent components that are either absorbed by the tissue of the body or expelled from the body. The biodegradation is accomplished by hydrolysis of the biodegradable material or through enzymatic action, as examples. In any regard, the biodegradable plug 22 is configured to "go away" after a predetermined amount of time from implantation into the body. As examples, suitable biodegradable materials include polyglycolic acid, polylactic acid, collagen, or a polymer combination of polyglycolic and polylactic acid (sometimes represented as PGA/PLA). The collagen source may be a human source or an animal source. The substantially uniform wall thickness T allows all portions of the plug 24 to degrade uniformly, e.g., at the same time.

With reference to FIG. 2, in one embodiment the plug 22 is provided as a shell with a wall thickness T in the region of the apex 34 is thicker than the wall thickness T in the region of the base 32, which provides the plug 22 with more material near the apex 34, thus strengthening the apex 34 at a location where the anchor 26 (FIG. 1) is attached.

The plug 22 is shaped to mate inside of the interior apical cuff of a vagina and includes a width Wb at the base 32 that is wider than a width Wa at the apex 34. It is desirable that the plug 22 conforms to the inside surface of the vagina and yet accommodate activities such as intercourse. In one suitable example of this style of plug, the plug 22 is provided with a recess or open cavity 40 that is configured to accommodate sexual activity. In addition, the recess 40 provides an engagement feature that allows an insertion tool to engage with the plug 22 when placing the plug 22 into the vagina.

The plug 22 has a through-going hole 42 formed through the wall 30 in the region of the apex 34. The hole 42 is sized to receive an end portion of the anchor 26 (FIG. 1). One hole 42 is illustrated, but other useful embodiments include two or more through-going holes 42 formed in the apex 34.

Figure 3A:
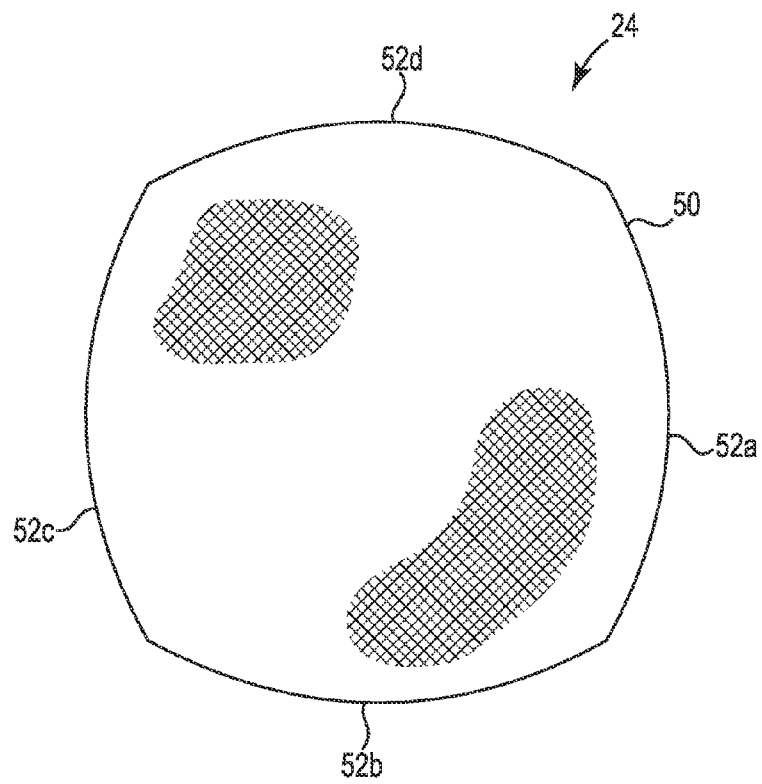
FIG. 3A is a top view of one embodiment of a flat skirt of the system illustrated in FIG. 1.

FIG. 3A is a top view of one embodiment of the skirt 24. The skirt 24 is a thin, flexible, and drapeable fabric-like material having a perimeter 50. The skirt 24 is configured to conform to the inside apical surface of the vagina and drape freely and uniformly over the plug 22 (FIG. 2). Suitable embodiments include the skirt 24 formed of fabric or of a film of a selected thickness that allows the skirt 24 to drape freely away from the plug 22 when the plug 22 and the skirt 24 are implanted in a patient.

In one embodiment, the skirt 24 is fabricated from an elastic material that will stretch and fit between the plug 22 and the apex of the vagina. In one embodiment, the perimeter 50 forms a substantially circular shape and the skirt 24 is fabricated from a sufficiently elastic material that allows the circular skirt 24 to be conformed to the hemispherical shape of the plug 22. In one embodiment, the perimeter 50 is formed by combination of arcs 52a, . . . 52d, the combination of which allows the skirt 24 to conform or be fitted into the interior apex of the vagina.

In one embodiment, the skirt 24 is formed from autograft material (the patient's own tissue), allograft material (tissue from a cadaver), xenograft material (tissue from another species), or synthetic material such as woven fabrics, meshes, nonwoven fabrics, or fibrous sheets. In one embodiment, the skirt 24 is porous and has openings or voids (pores) that are configured to allow tissue ingrowth into the skirt 24. The pores are open areas that are generally larger, on average, than 75 μm. In one suitable example, the skirt 24 is a knitted polypropylene mesh with a basis weight of between 15-200 g/m² and an open pore structure where at least some of the pores have an open dimension between 60-300 μm.

In one suitable example, the skirt 24 is a biodegradable fabric having a basis weight of between 15-200 g/m² and an open pore structure where at least some of the pores have a dimension between 60-300 μm.

In one embodiment, the skirt 24 is integrated with the plug 22 to provide a monolithic plug-skirt component. For example, a central portion of the skirt 24 is connected/integrated with the plug 22 to provide a one-piece plug and skirt implantable component.

Figure 3B:
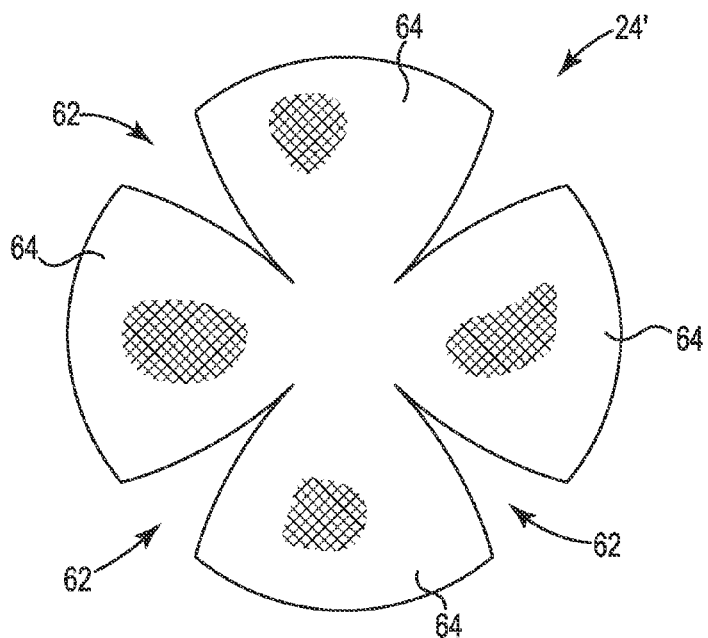
FIG. 3B is a top view of one embodiment of a different flat skirt of the system illustrated in FIG. 1.

FIG. 3B is a top view of one embodiment of another skirt 24' suited for use with the system 20 (FIG. 1). The skirt 24' has an outside edge perimeter provided with relief portions 62 that are configured to allow the skirt 24' to conform to the curved inside (concave) surface of the vagina and the curved exterior (convex) surface of the plug 22 (FIG. 2). The relief portions 62 provide the skirt 24' with petals 64 that allow the skirt 24' to drape uniformly over the curved three-dimensional surface of the plug 22 without forming puckers or gathers of material in the skirt 24', which ensures that the plug 22 uniformly presses the skirt 24' against the interior apical cuff of the vagina when implanted.

Figure 3C:
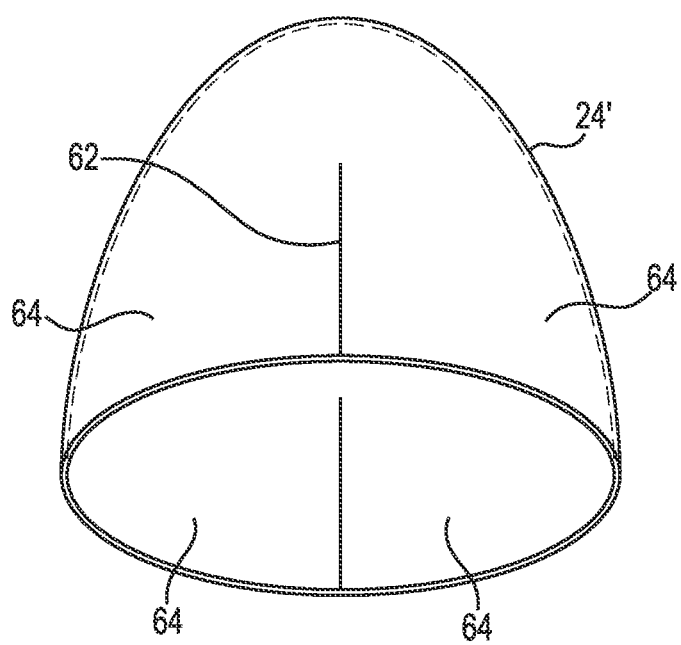
FIG. 3C is a perspective view of the flat skirt illustrated in FIG. 3B formed into a hollow three-dimensional shell.

FIG. 3C is a perspective view of the flat skirt 24' illustrated in FIG. 3B formed into a hollow three-dimensional shell suitable for placement anterior to the apex of the vagina.

Figure 4:
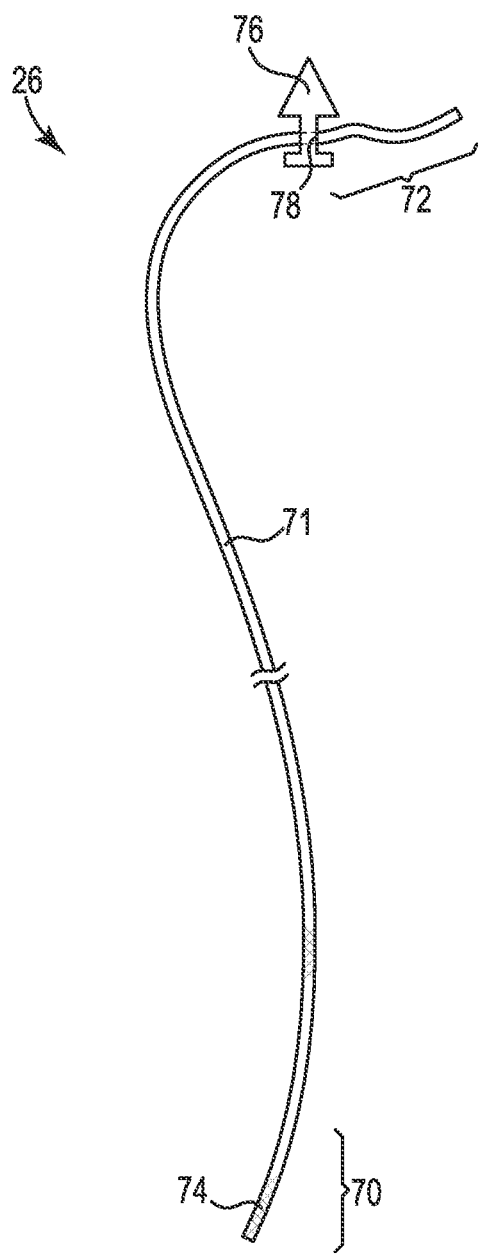
FIG. 4 is a perspective view of one embodiment of an anchor of the system illustrated in FIG. 1.

FIG. 4 is a perspective view of one embodiment of the anchor 26. The anchor 26 includes a strand 71 provided with a proximal portion 70 and a distal portion 72. The proximal portion 70 is attachable the plug 22 and the skirt 24 (FIG. 1). In one embodiment, the proximal portion 70 is inserted through the skirt 24 and through the hole 42 (FIG. 2) formed in the plug 22. The proximal portion 70 is suitably fixated upon implantation by attachment to tissue of the vagina or by suturing to the plug 22. In one embodiment, the proximal portion 70 includes a reinforced area 74 that is tear-resistant and configured to resist the stress of sutures or other attachments mechanisms that are employed to secure the proximal portion 70 of the anchor 26 to the plug 22/skirt 24.

The distal portion 72 of the anchor 26 is attachable to supporting tissue of the patient, such as the tissue surrounding the sacrum or to ligaments within the pelvis. In one embodiment, the distal portion 72 includes a fixation device 76 that is insertable into the supporting tissue. Embodiments of the fixation device 76 provide for adjustment of the anchor 26, for example by sliding the distal portion 72 of the anchor 26 though a slot 78 or opening formed in the fixation device 76. Adjustment of the strand 71 relative to the fixation device 76 allows the tension in the anchor 26 to be adjusted and also allows the distance between the proximal portion 70 and the fixation device 76 to be shortened/lengthened. In one embodiment, the strand 71 has a length of between about 2-16 cm, which allows the strand 71 to be sized to fit between the apex of the vagina and the sacrum for a variety of differently sized patients. The excess portion of the strand 71 that is pulled through the slot 78 of the fixation device 76 may be removed after implantation.

In one embodiment, all of the components of the anchor 26 are biodegradable and are formed from, as examples, polyglycolic acid, or polylactic acid, or a polymer combination of polyglycolic and polylactic acid. In one embodiment, the anchor 26 is not biodegradable and is formed of a polypropylene mesh strand 71 attached to a non-biodegradable, plastic fixation device 76. In one embodiment, the anchor 26 is provided as a strip of collagen without the optional fixation device 76, and the strip of collagen is sutured at the proximal end 70 to the plug 22 and sutured at the distal end 72 to the tissue surrounding the sacrum.

Figure 5A:
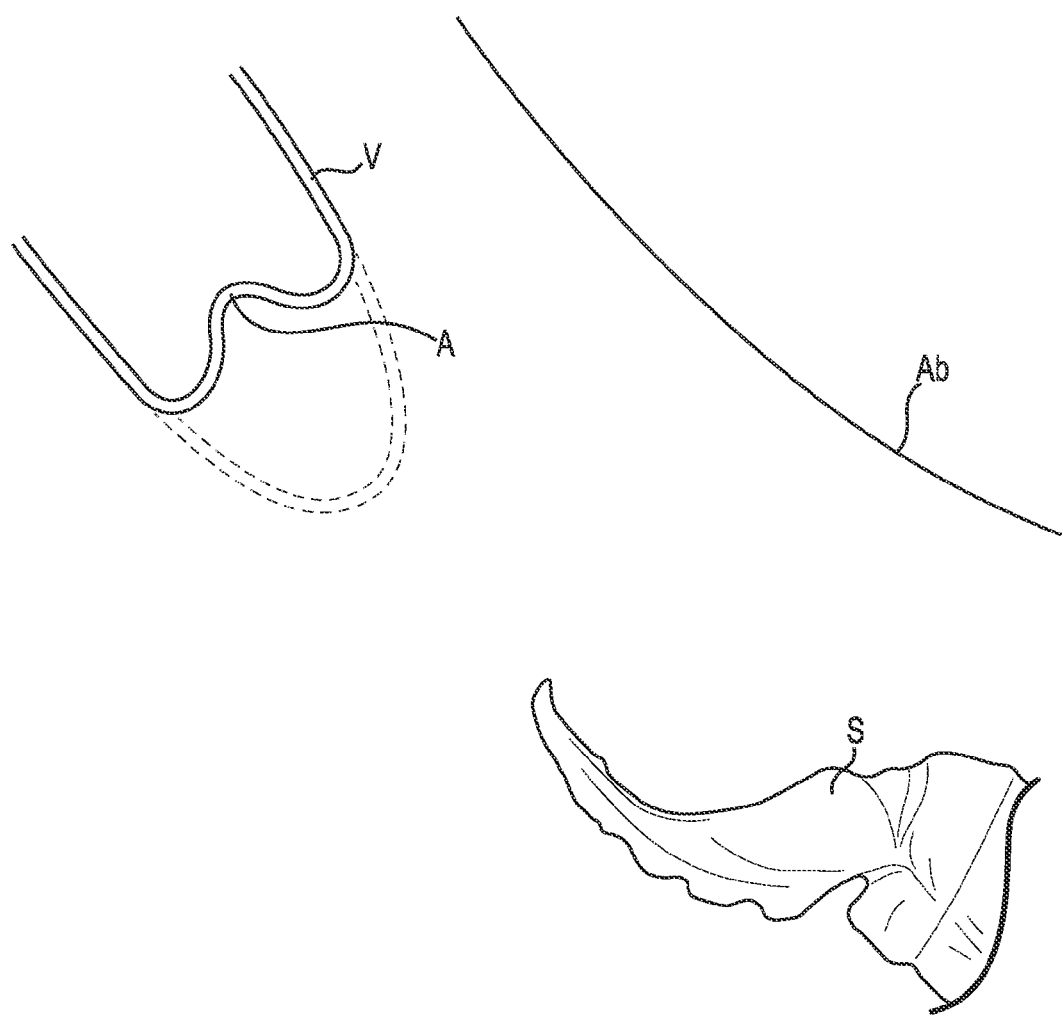
FIG. 5A is a schematic view of a patient with a prolapsed vagina.
Figure 5B:
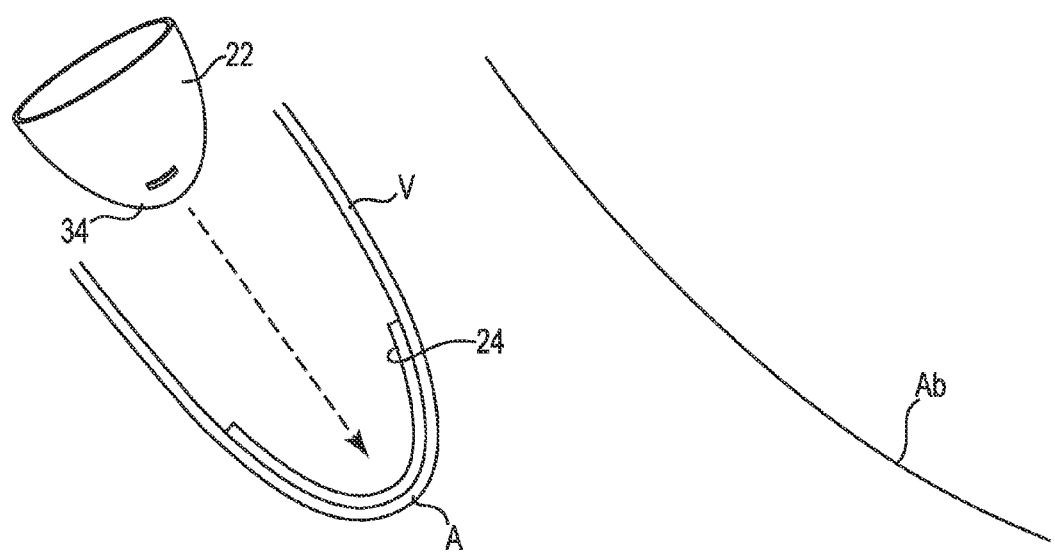
FIG. 5B is a schematic view of one embodiment for the placement of the skirt inserted into the vagina.
Figure 5B:
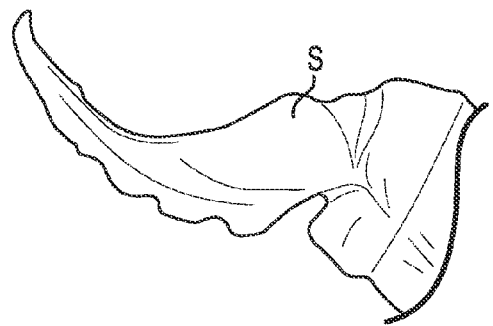
Figure 5C:
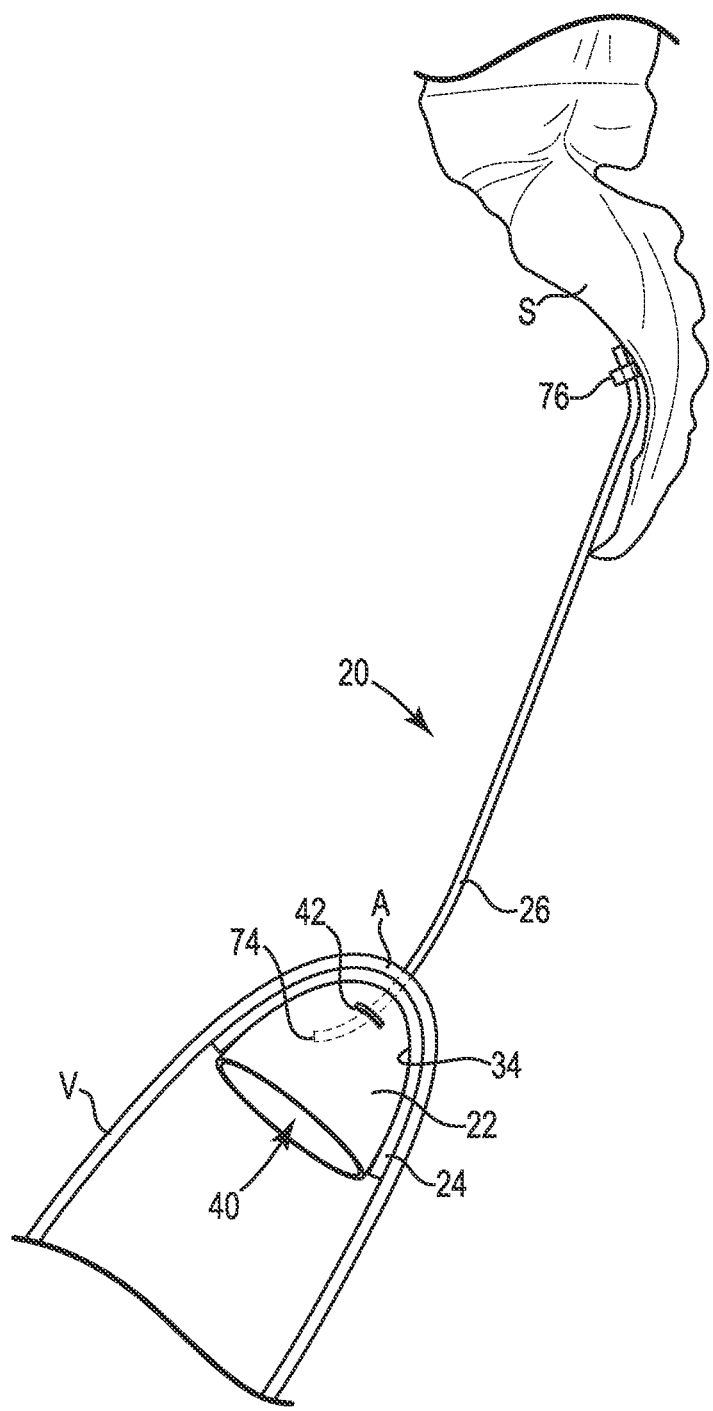
FIG. 5C is a schematic view of one embodiment of the system illustrated in FIG. 1 implanted in the patient.

FIGS. 5A-5C illustrate the system 20 employed to treat a prolapsed vagina V.

FIG. 5A is a schematic view of a patient positioned in a lithotomy position, or an elevated lithotomy position, with the pelvis elevated above the head. The patient's vagina V has undesirably prolapsed and presents with an apex A of the vagina V that has descended from its natural position. The sacrum S is illustrated relative to the patient's abdomen Ab. Treatment of the prolapsed vagina V includes supporting and maintaining the apex A of the vagina V in its natural position, for example through attachment to ligaments or other structures in the pelvis or through attachment to the sacrum S.

FIG. 5B is a schematic view of the skirt 24 placed in an interior apical portion A of the vagina V. In one approach, the skirt 24 is inserted into the vagina V through the natural vaginal opening without forming an incision. The skirt 24 is placed on the interior surface of the vagina V to support and maintain the natural extended position of the apex A of the vagina V. The plug 22 is subsequently inserted into the vagina V to support the skirt 24 and to ensure that the skirt 24 remains in contact with the tissue along the interior surface of the vagina V. FIG. 5C is a schematic view of the system 20 implanted in the patient.

The skirt 24 is held in contact with the interior apical tissue of the vagina V through the placement of the plug 22, and the plug 22 and the skirt 24 are supported in position by the anchor 26 that is connected between the plug 22 and the sacrum S. In one exemplary approach, the proximal portion 74 of the anchor 26 projects through the wall of the vagina V and the skirt 24 and is inserted through the hole 42 of the plug 22. The surgeon may elect to place a suture through the proximal portion 74 of the anchor 26 into the interior tissue of the vagina. The opposite end of the anchor 26 is attached to the sacrum S, for example by the fixation device 76. Excess material in the strand 71 that is located distal of the fixation device 76 is removed. In one embodiment, the plug 22/skirt 24 are placed into the vagina and the anchor 26 is implanted in the patient, for example laparoscopically in a transabdominal approach.

The apex 34 of the plug 22 is shaped to conform to the natural curvature of the apex A of the vagina V. In one embodiment, the plug 22 is provided as a biodegradable thin-walled shell of material that encourages and maintains contact between the skirt 24 and the tissue the vagina V. The plug 22 is configured to biodegrade away and out from the vagina leaving the skirt 24 incorporated into and supporting the tissue at the apex A of the vagina V. For embodiments where the skirt 24 is not biodegradable, the skirt 24 will be incorporated into the tissue of the vagina V, for example through tissue ingrowth into the skirt 24. For embodiments where the skirt 24 is biodegradable, both of the plug 22 and the skirt 24 will biodegrade away from the vagina leaving the repaired and strengthened apex A of the vagina V supported by the anchor 26.

FIG. 5C illustrates the patient in an upright position with the apex A of the vagina supported by the system 20. The plug 22 holds the skirt 24 in position until the tissue of the vagina V grows through the porous structure of the skirt 24. The recess 40 formed in the plug 22 is configured to allow the patient to resume normal activity, including intercourse. The plug 22 is configured to degrade away out of the body after an appropriate and selected amount of time sufficient to allow tissue ingrowth to the skirt 24. Thereafter, the skirt and the anchor 26 combine to support the apex 34 of the vagina V. In this embodiment, a system 20 for treating pelvic organ prolapse includes a porous sheet of material in the form of the skirt 24; the anchor 26 having the proximal portion 74 that is attachable to the porous skirt 24 and a distal portion that is provided with the tissue fixation device 76; and means in the form of the plug 22 for maintaining the porous skirt 24 in contact with an interior apical portion of a vagina. The plug 22 maintains an entirety of a surface area of at least one side of the porous skirt 24 in contact with the interior portion of a vagina.

In one embodiment, both the plug 22 and the skirt 24 eventually biodegrade away from the body leaving the anchor 26 attached between the sacrum S and the repaired and strengthened apex A of the vagina. In one such example, the plug 22 is made of a first biodegradable material having a first rate of degradation and the skirt 24 is made of a second biodegradable material having a rate of degradation different from the first rate of degradation. This allows both the plug 22 and the skirt 24 to eventually biodegrade away from the body, but at different rates (and thus at different times).

In one embodiment, all of the components of the system 20 are selected to be biodegradable. The system 20 is implanted into the patient to encourage tissue ingrowth into the skirt 24 and the anchor 26. The tissue growth is substantial and will support the vagina, and in this sense all of the components of the system 20 are allowed to biodegrade and the vagina will be supported by the new tissue that has grown into place.

For example, the plug 22 is fabricated of a first biodegradable material, the anchor 26 is fabricated of a second biodegradable material, and the skirt 24 is fabricated of a third biodegradable material, where each of the biodegradable materials is suitably selected to have a different rate of degradation. The biodegradation of any one of the components is a factor of the mass of the biodegradable component, the selected biodegradable material and its rate of biodegradation, and the thickness of the material. These factors may be adjusted to achieve a desired time of degradation for each component individually.

The different rates of degradation allow, for example, the skirt 24 to remain in place within the vagina V for a longer period of time than the plug 22, and after suitable incorporation into the tissue of the vagina, the skirt 24 biodegrades away leaving the anchor 26 supporting the apex A of the vagina. Embodiments provide for the eventual biodegradation of the anchor 26 after the apex A of the vagina has been repaired and strengthened by the system 20.

FIGS. 6A-8 illustrate other means for maintaining the porous skirt 24 in contact with an interior apical portion of a vagina.

Figure 6A:
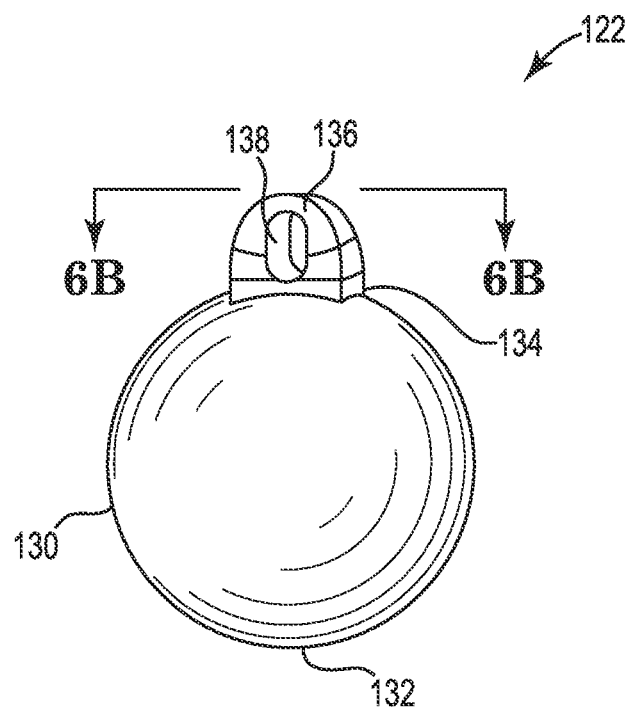
FIG. 6A is a perspective view of one embodiment of a plug suitable for use with the system illustrated in FIG. 1.
Figure 6B:
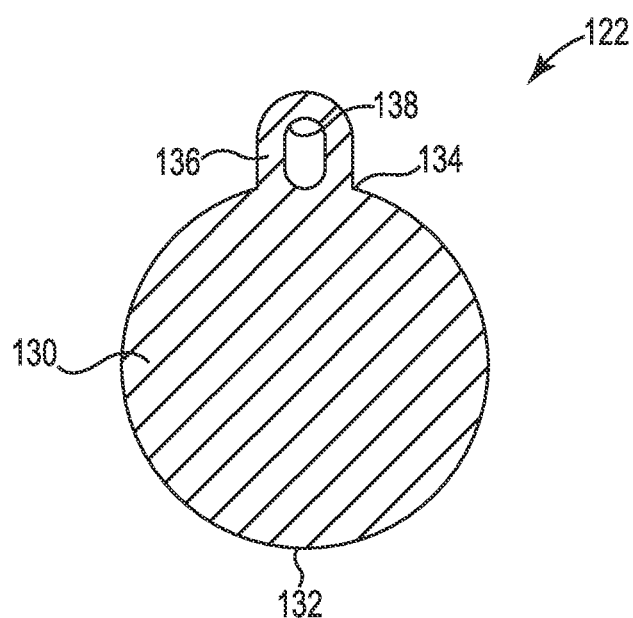
FIG. 6B is a cross-sectional view of the plug illustrated in FIG. 6A.

FIG. 6A is a perspective view and FIG. 6B is a cross-sectional view of one embodiment of a plug 122 suitable for use with the system 20 illustrated in FIG. 1. The plug 122 includes a body 130 extending from a base 132 to a shoulder 134 with an apex 136 extending from the shoulder 134. In contrast to the hollow hemispherical cap 22 described above, embodiments of the plug 122 provide the body 130 formed as a substantially solid sphere of biodegradable material. The shoulder 134 is provided opposite the base 132 and the apex 136 extends away from the shoulder 134. The plug 122 is configured for insertion into the interior apical region of the vagina, and the apex 136 is designed to penetrate through the vaginal wall. The body 130 is provided with a lateral dimension that is wider than a lateral dimension of the apex 136. In one embodiment, the apex 136 is formed to include a through-going hole 138 that allows the plug 122 to engage with an anchor device, such as the anchor 26 described in FIG. 4 above.

Figure 7A:
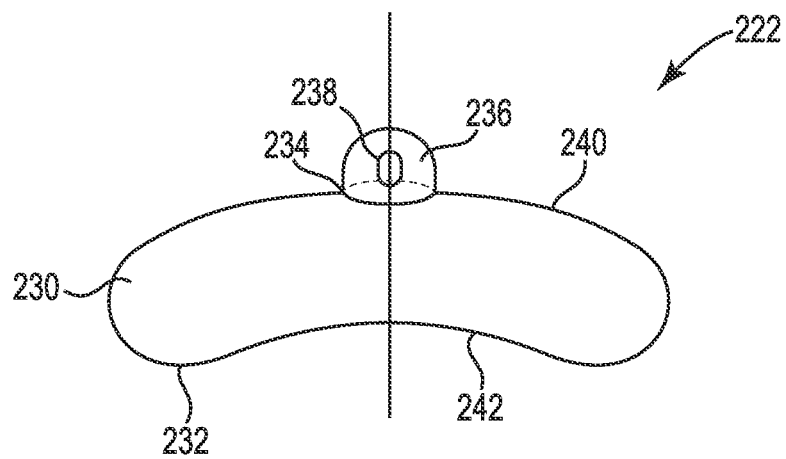
FIG. 7A is a perspective view of one embodiment of a different plug suitable for use with the system illustrated in FIG. 1.
Figure 7B:
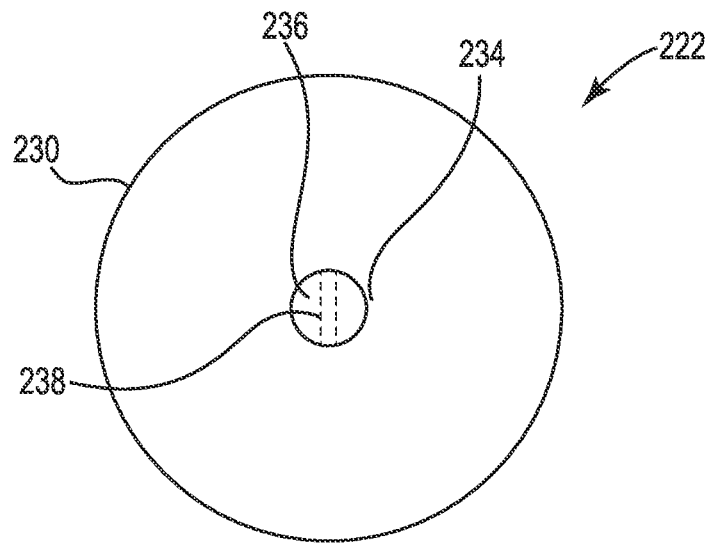
FIG. 7B is a top view of the plug illustrated in FIG. 7A.

FIG. 7A is a perspective view and FIG. 7B is a top view of one embodiment of a plug 222 suitable for use with the system 20 illustrated in FIG. 1. The plug 222 includes a body 230 extending from a base 232 to a shoulder 234 with an apex 236 extending from a shoulder 234. In one embodiment, the body 230 is formed as a substantially solid kidney shaped disk that includes a curved convex distal surface 240 and a curved concave proximal surface 242. The apex 236 extends from the shoulder 234 and is configured to penetrate through the wall of the vagina with the body 230 supporting the interior apical portion inside of the vagina. The apex 236 includes a through-going hole 238 that is provided for engagement with an anchor or other fixation device.

Figure 7C:
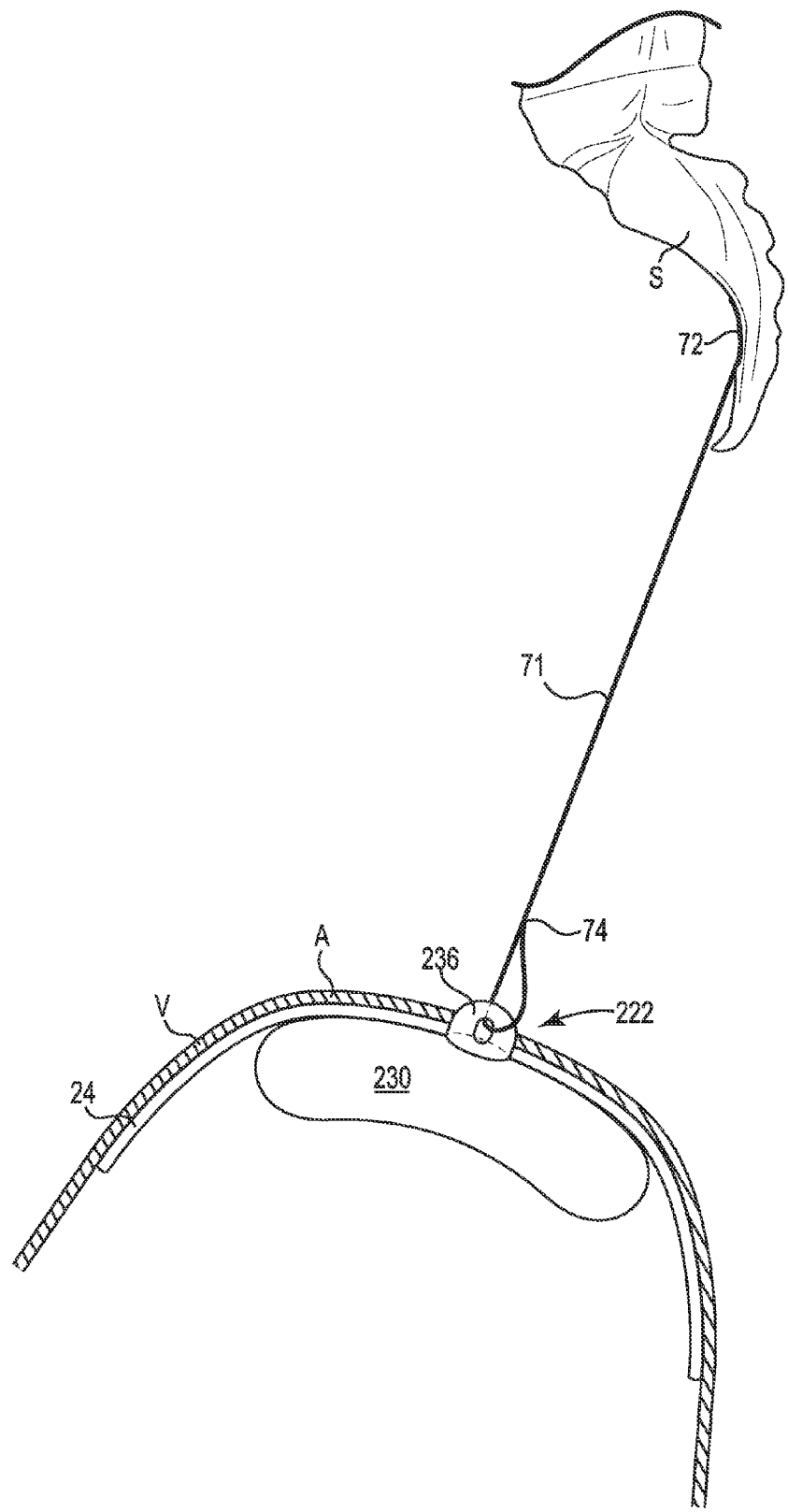
FIG. 7C is a schematic cross-sectional view of the plug illustrated in FIG. 7A implanted in the patient.

FIG. 7C is a schematic cross-sectional view of the plug 222 implanted in a vagina to hold the skirt 24 in contact with the interior tissue of the vagina V. The strand 71 described above is attached at one end to the plug 222 and secured at an opposing end to the sacrum S. In one embodiment, the apex 236 of the plug 222 projects through the apex A of the vagina for attachment to the strand 71. The body 230 of the plug 222 distributes the supporting force across a wide area of the apex A of the vagina V.

In one embodiment, the skirt 24 is a biodegradable skirt and the plug 222 and the anchor strand 71 are not biodegradable. In this manner, the skirt 222 is absorbed into the wall of the vagina V leaving the anchor strand 71 applying an upward supporting force to the plug 222, which elevates the apex A of the vagina V.

Figure 8:
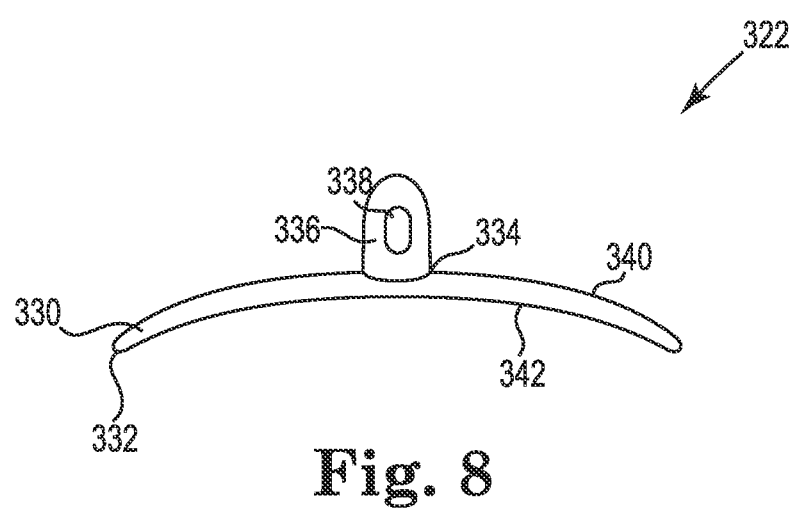
FIG. 8 is a side view of one embodiment of a different plug suitable for use with the system illustrated in FIG. 1.

FIG. 8 is a side view of one embodiment of a plug 322 suitable for use with the system 20 illustrated in FIG. 1. The plug 322 includes a body 330 extending from a base 332 to a shoulder 334 with an apex 336 extending from the shoulder 334. In one embodiment, the body 230 is formed as a thin-walled circular hanger that includes a curved convex distal surface 340 and a curved concave proximal surface 342. The apex 336 extends from the shoulder 334 and is configured to penetrate through the wall of the vagina with the body 330 supporting the interior apical portion inside of the vagina. The apex 336 includes a through-going hole 338 that is provided for engagement with an anchor or other fixation device.

Figure 9A:
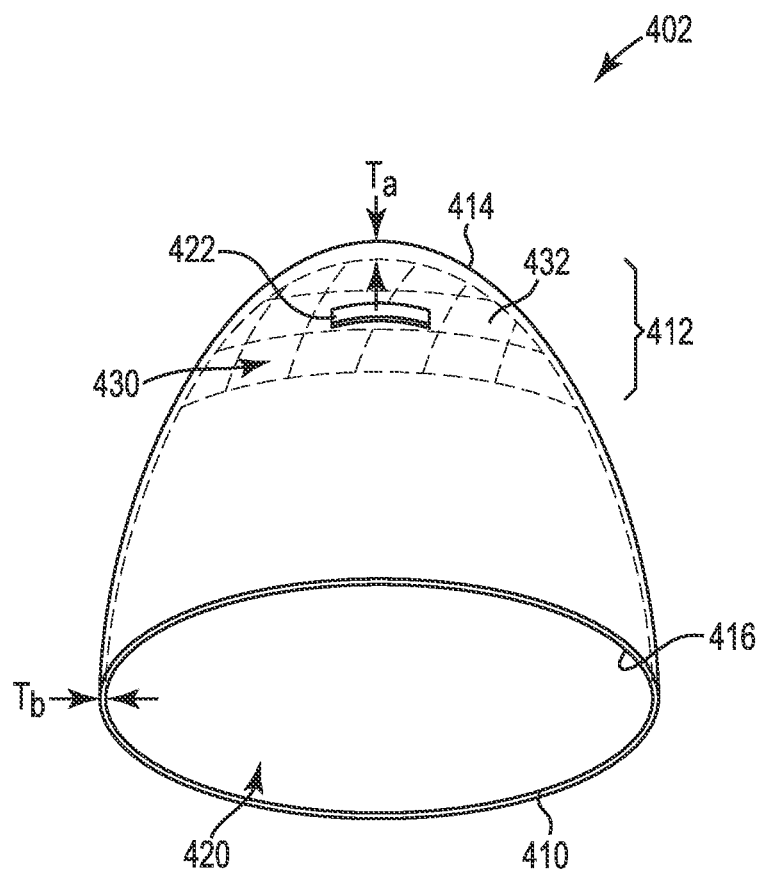
FIG. 9A is a perspective view of one embodiment of a support shell for use in a system for treating pelvic organ prolapse.

FIG. 9A is a perspective view of one embodiment of a support shell 402 for use in a system for treating pelvic organ prolapse. The shell 402 is provided as a thin-walled structure having a base 410 and a convex exterior apex 412. The apex 412 includes a convex exterior 414 that is sized to contact an interior apical portion of the vagina. The shell 402 includes a concave interior portion 416 on a side opposite from the convex exterior 414, and in one embodiment the shell 402 is a substantially hollow hemispherical cap provided with an open base portion 420. The shell 402 includes an attachment feature 422 on the convex exterior apex 412 that is configured to couple with an anchor device, for example the anchor device 26 illustrated in FIG. 4.

In one embodiment, the shell 402 has a wall thickness Tb at the base 410 that is less than a wall thickness Ta of the apex, which configures the shell 402 to have more mass at the apex 412. The shell 402 encourages tissue growth from the wall of the vagina into the shell 402, which strengthens and supports the vaginal apex. In one embodiment, the shell 402 is biodegradable and absorbs or disintegrates after the vaginal tissue has grown in the region of the vaginal apex. The tissue growth at the vaginal apex strengthens that region of the vagina, which allows the anchor to better support the vagina. While not bound to this theory, it is thought that providing the apex 412 of the shell 402 with more mass compared to the base that improved support is provided to the apical portion of the vagina, particularly as the thinner base 410 will biodegrade/bioabsorb ahead of the thicker apex 412.

In one embodiment, a region 430 of the apex 412 is reinforced to provide added strength to the apex 412 of the shell 402. Suitable reinforcing structures include providing a net or screen or mesh that is encapsulated in a wall 432 of the shell 402. The net or screen or mesh couples with the anchor and can be configured as biodegradable or non-biodegradable. Another suitable reinforcing structure includes a waffle pattern pressed into the wall 432 of the shell 402.

In one embodiment, the exterior of the shell 402 is textured and so configured to allow tissue of the vagina to grow into the shell 402.

In one embodiment, the apex 412 of the shell 402 is porous and so configured to allow tissue of the vagina to grow into the shell 402.

In one embodiment, the apex 412 of the shell 402 has a plurality of open areas and is so configured to allow tissue of the vagina to grow into the shell 402.

In one embodiment, the shell 402 is fabricated from collagen and is configured to biodegrade after implantation into the human body.

Figure 9B:
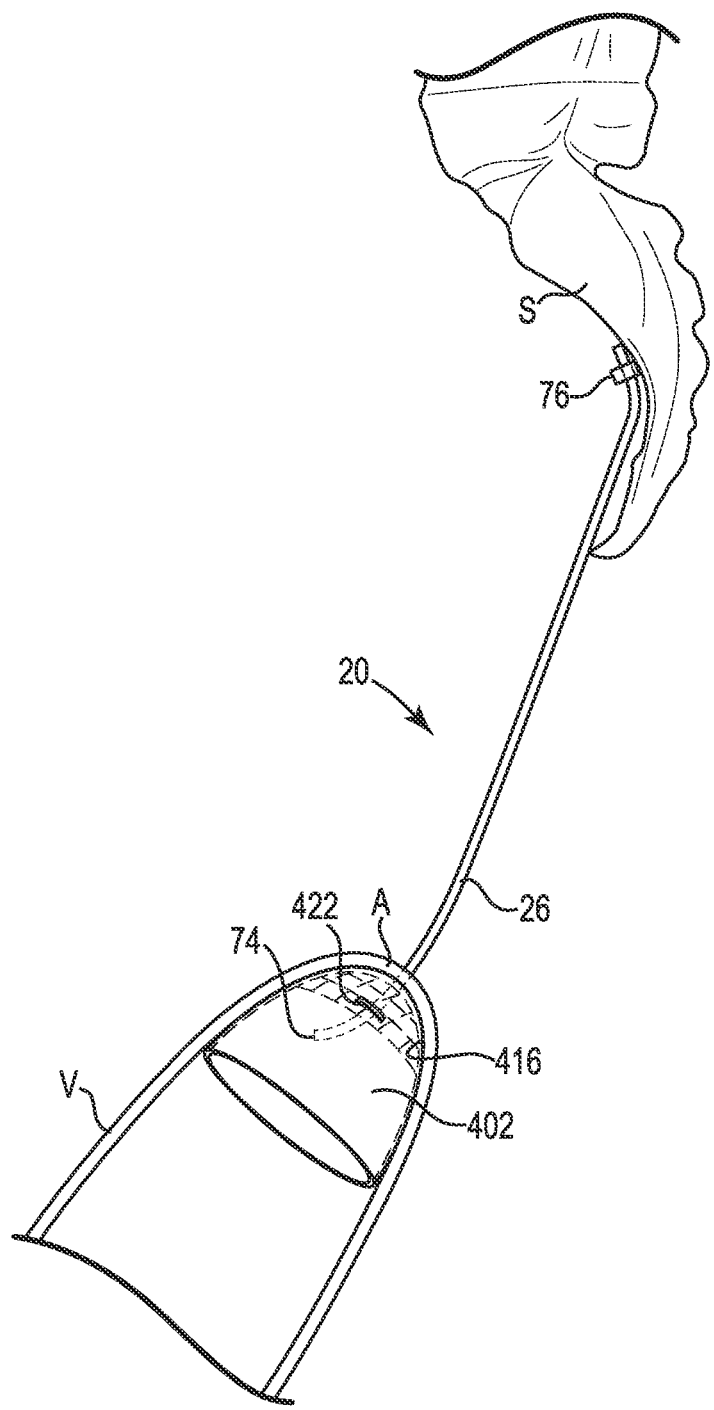
FIG. 9B is a schematic view of one embodiment of the support shell illustrated in FIG. 9A implanted in the patient.

FIG. 9B illustrates the patient in an upright position with the apex A of the vagina supported by the implanted shell 402. The shell 402 supports the vagina V in position until the tissue of the vagina V grows in place in the apical region of the vagina V.

The shell 402 is supported by, for example, the anchor 26 (FIG. 4). The anchor 26 has the proximal portion 74 attached to the attachment feature 422 and the distal portion with the tissue fixation device 76 is secured to support tissue, for example, the sacrum S. The anchor 26 and the shell 402 combine to support and elevate the interior apical portion of the vagina V. Eventually, the shell 402 is either absorbed into the body or disintegrates away, leaving the apex A of the vagina V strengthened by tissue growth in the apical region of the vagina. The strengthened tissue near the apex of the vagina is well suited for allowing the anchor 26 to elevate the apex A of the vagina V. supported by the anchor 26.

Although specific embodiments have been illustrated and described in this patent application, it will be appreciated by those of ordinary skill in the art that a variety of alternate and/or equivalent implementations may be substituted for the specific embodiments shown and described without departing from the scope of the invention. This patent application is intended to cover any adaptations or variations of medical devices, as discussed above. Therefore, it is intended that this invention be limited only by the claims and their equivalents.

What is claimed is:

1. A method of treating prolapse of a vagina, the method comprising:
   inserting a shell into the vagina;
   contacting a convex exterior apex of the shell with an interior apical portion of the vagina associated with an apex of the vagina; and
   securing a first portion of an anchor to the shell and securing a second portion of the anchor to one of a ligament and a sacrum exterior to and separate from the vagina, thus supporting the apex of the vagina relative to the ligament or the sacrum.

2. The method of claim 1, comprising inserting a hollow shell into the vagina.

3. The method of claim 1, comprising contacting a textured convex exterior apex of the shell with the interior apical portion of the vagina.

4. The method of claim 1, comprising contacting a porous convex exterior apex of the shell with the interior apical portion of the vagina.

5. The method of claim 1, wherein the convex exterior apex of the shell is provided with open areas formed through the shell, the method comprising contacting the open areas of the shell with the interior apical portion of the vagina and encouraging tissue to grow through the open areas of the shell.

6. The method of claim 1, comprising inserting a shell fabricated from collagen into the vagina.

7. The method of claim 1, comprising inserting a biodegradable shell into the vagina.

8. The method of claim 1, comprising inserting a hemispherically shaped shell into the vagina.

9. The method of claim 1, wherein the convex exterior apex of the shell is strengthened with a reinforcement structure providing the shell with a reinforced convex exterior apex, and the method further comprising:
   contacting the interior apical portion of the vagina with the reinforced convex exterior apex of the shell.

10. The method of claim 1, wherein the shell includes a reinforcement structure encapsulated into the convex exterior apex of the shell providing the shell with a reinforced convex exterior apex, and the method further comprising:
    contacting the interior apical portion of the vagina with the reinforced convex exterior apex of the shell.

11. The method of claim 1, wherein the shell includes a biodegradable reinforcement structure encapsulated into the convex exterior apex of the shell providing the shell with a biodegradable reinforced convex exterior apex, and the method further comprising:
    contacting the interior apical portion of the vagina with the biodegradable reinforced convex exterior apex of the shell.

12. The method of claim 1, wherein the convex exterior apex of the shell is strengthened with a patterned reinforcement structure pressed into the shell providing the shell with a patterned reinforced convex exterior apex, and the method further comprising:
    contacting the interior apical portion of the vagina with the patterned reinforced convex exterior apex of the shell.

13. The method of claim 1, comprising securing the first portion of the anchor to an attachment feature provided on the convex exterior apex of the shell.

14. The method of claim 1, wherein the shell comprises a skirt and a plug separate from the skirt, the method comprising:
  inserting the skirt into the vagina;
  contacting the interior apical portion of the vagina with the skirt;
  inserting the plug into the vagina;
  contacting the skirt with the plug; and
  securing the first portion of the anchor to the plug.

15. The method of claim 14, wherein the skirt has an outside edge perimeter provided with relief portions that are configured to allow the skirt to conform to curvature of the vagina, the method comprising:
  draping the skirt over an exterior surface of the plug; and
  inserting the skirt and the plug into the vagina.

16. The method of claim 1, comprising inserting the shell into the vagina by providing the shell as a biodegradable plug separate from a skirt, and:
  inserting the skirt into the vagina; and
  pressing the skirt against the interior apical portion of the vagina with the biodegradable plug.

17. The method of claim 1, comprising inserting the shell into the vagina by providing the shell as a biodegradable plug separate from a biodegradable skirt, and:
  inserting the biodegradable skirt into the vagina; and
  pressing the biodegradable skirt against the interior apical portion of the vagina with the biodegradable plug.

18. The method of claim 1, comprising:
  inserting the shell into the vagina through a natural opening of the vagina; and
  securing the first portion of the anchor to the shell and securing the second portion of the anchor to the ligament or the sacrum laparoscopically.

* * * * *